(12) United States Patent
Ricci

(10) Patent No.: US 8,057,428 B2
(45) Date of Patent: Nov. 15, 2011

(54) STENT DELIVERY SYSTEM AND METHOD OF USE

(75) Inventor: Donald R. Ricci, Vancouver (CA)

(73) Assignee: Evysio Medical Devices ULC (CA)

( * ) Notice: Subject to any disclaimer, the term of this patent is extended or adjusted under 35 U.S.C. 154(b) by 307 days.

(21) Appl. No.: 12/497,212

(22) Filed: Jul. 2, 2009

(65) Prior Publication Data

US 2009/0270905 A1 Oct. 29, 2009

Related U.S. Application Data

(63) Continuation of application No. 11/045,134, filed on Jan. 31, 2005, now abandoned, which is a continuation of application No. 09/780,940, filed on Feb. 12, 2001, now Pat. No. 6,849,077, which is a continuation-in-part of application No. 09/557,007, filed on Apr. 20, 2000, now abandoned, which is a continuation-in-part of application No. 09/501,981, filed on Feb. 11, 2000, now abandoned.

(51) Int. Cl.
*A61M 29/00* (2006.01)
*A61F 11/00* (2006.01)

(52) U.S. Cl. .................. 604/96.01; 604/164.05; 606/108

(58) Field of Classification Search ............... 604/96.01, 604/103.01, 103.04, 103.05, 102.01, 102.02, 604/164.05, 915; 606/108, 192, 194, 198
See application file for complete search history.

(56) References Cited

U.S. PATENT DOCUMENTS

| | | | | |
|---|---|---|---|---|
| 4,748,982 A * | 6/1988 | Horzewski et al. | ........... | 606/192 |
| 5,161,534 A * | 11/1992 | Berthiaume | ........... | 600/434 |
| 5,334,187 A * | 8/1994 | Fischell et al. | ........... | 604/102.02 |
| 5,395,335 A * | 3/1995 | Jang | ........... | 604/102.02 |
| 5,458,613 A * | 10/1995 | Gharibadeh et al. | ........... | 606/194 |
| 5,490,837 A * | 2/1996 | Blaeser et al. | ........... | 604/103.11 |
| 6,007,522 A * | 12/1999 | Agro et al. | ........... | 604/264 |
| RE36,857 E * | 9/2000 | Euteneuer et al. | ........... | 604/102 |
| 6,355,013 B1 * | 3/2002 | van Muiden | ........... | 604/96.01 |
| 6,606,515 B1 * | 8/2003 | Windheuser et al. | ........... | 600/434 |

* cited by examiner

*Primary Examiner* — Nicholas D. Lucchesi
*Assistant Examiner* — Quynh-Nhu H Vu
(74) *Attorney, Agent, or Firm* — Katten Muchin Rosenman LLP

(57) ABSTRACT

A balloon dilation catheter comprising a tubular member having a proximal end and a distal end. An inflatable balloon is disposed at the distal end of the tubular member. A first lumen is disposed in the tubular member and in is communication with an interior of the inflatable balloon. A second lumen is disposed in the tubular member for receiving a guidewire substantially along a portion of its length. The second lumen has a first opening in the proximal region of the tubular member and a second opening at the distal region of the tubular member. A first slit is disposed longitudinally in the tubular member and extends along at least a portion of the tubular member, the first slit comprising a first pair of longitudinal edges in a side by side relationship. The tubular member is constructed of a resilient material such that, as the guidewire is separated from the second lumen, the longitudinal edges are biassed open from a first position to a second position having a gap greater than or equal a diameter of the guidewire. The subject balloon dilation catheter provides improved rapid exchange advantages of either the catheter or the guidewire used in a catheterization technique.

17 Claims, 9 Drawing Sheets

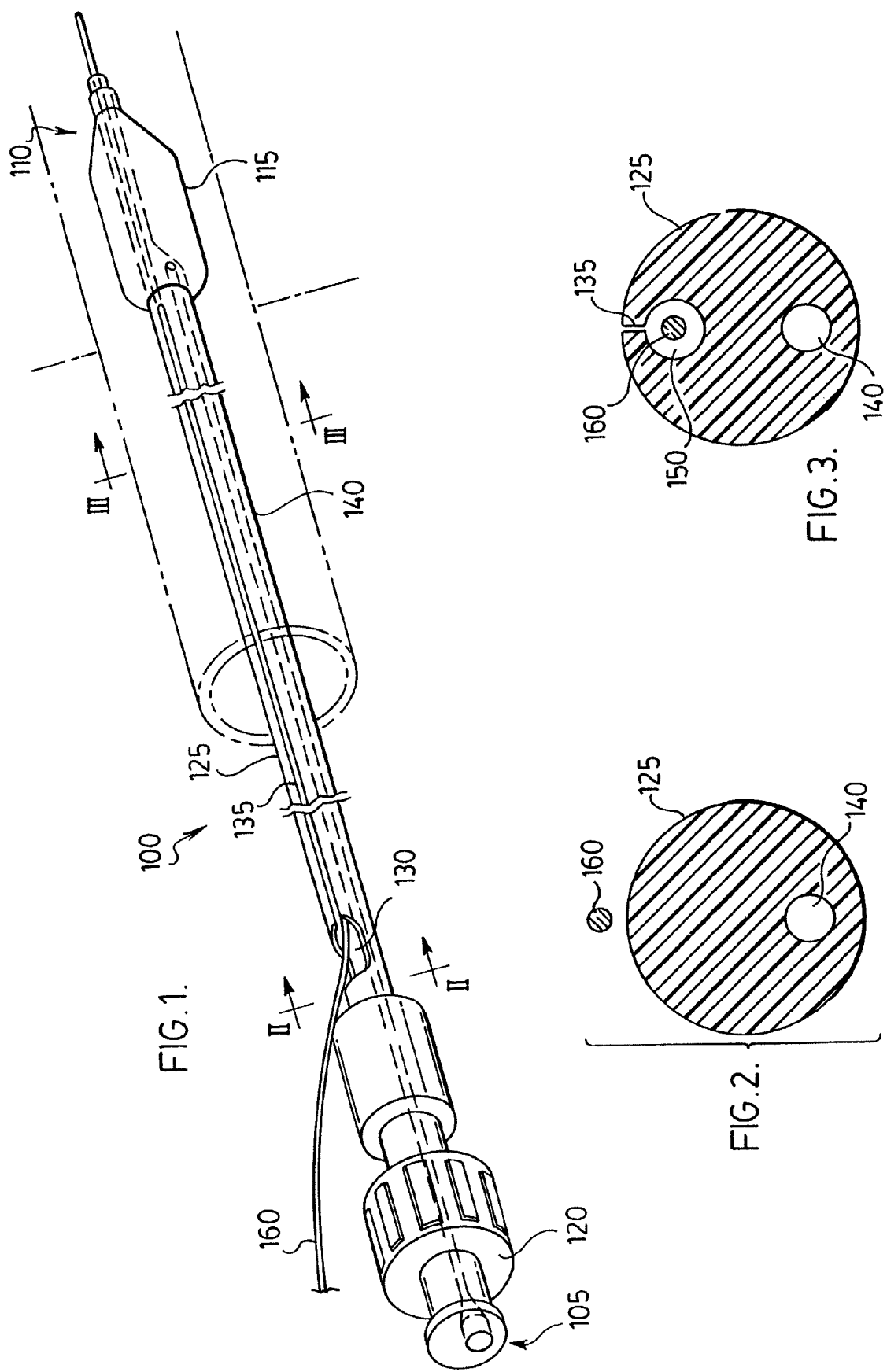

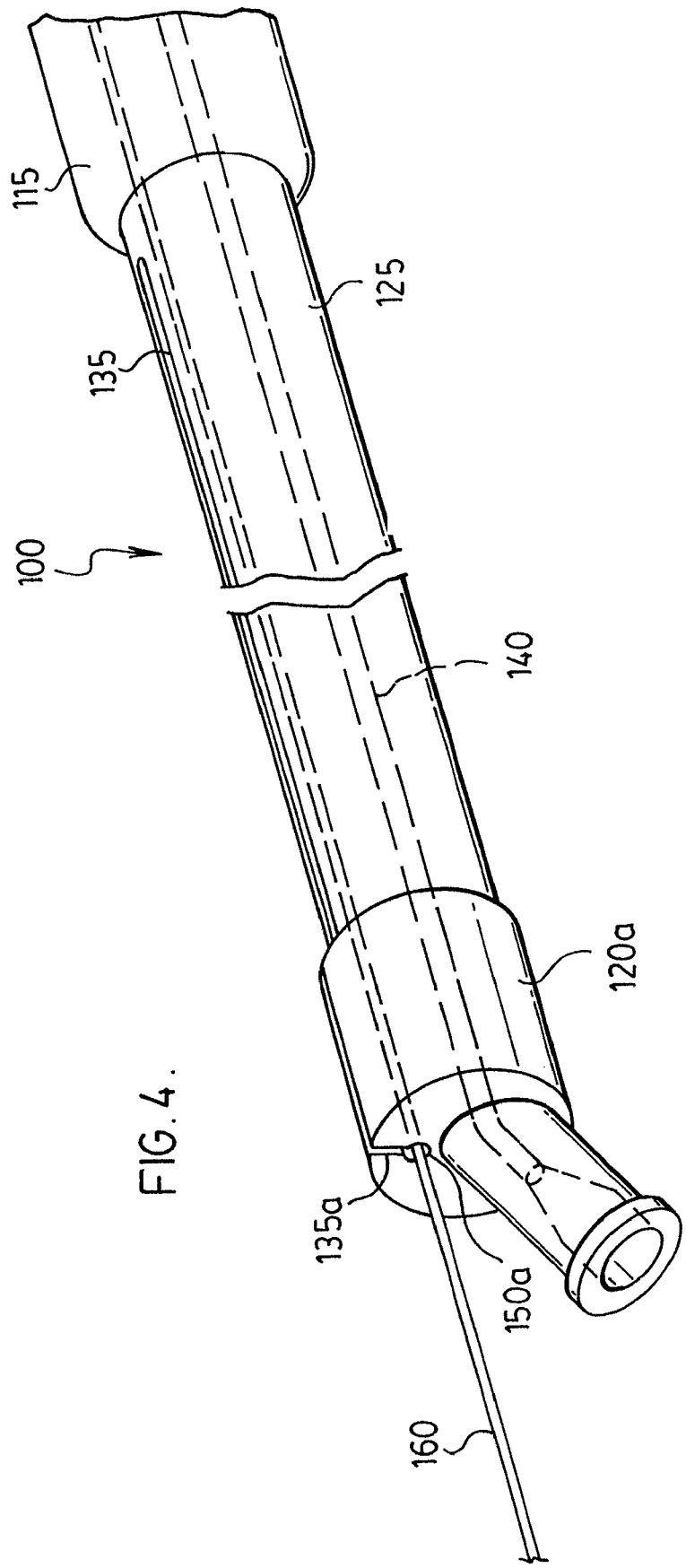

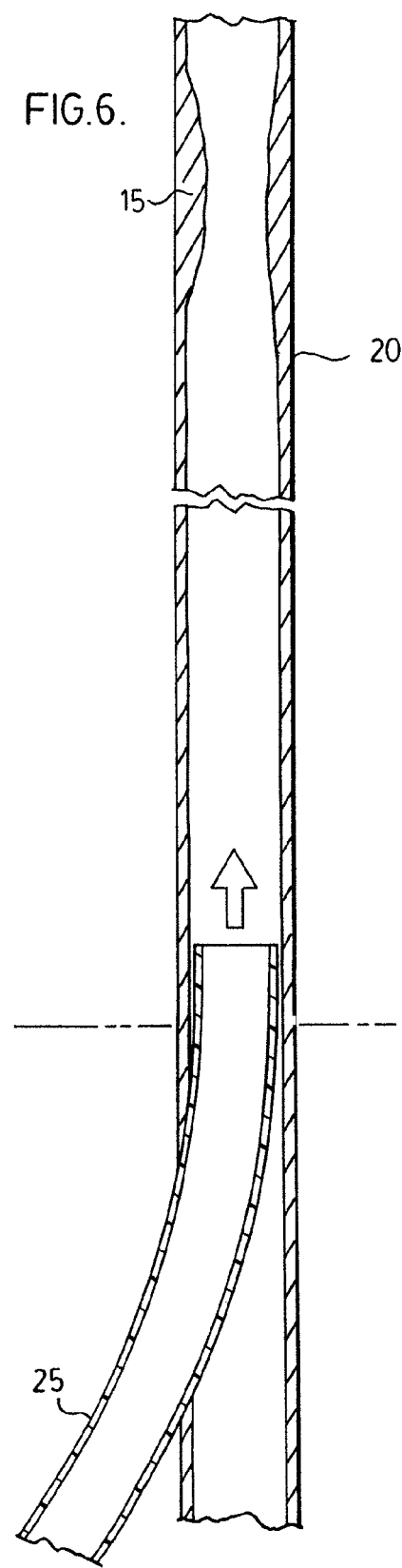
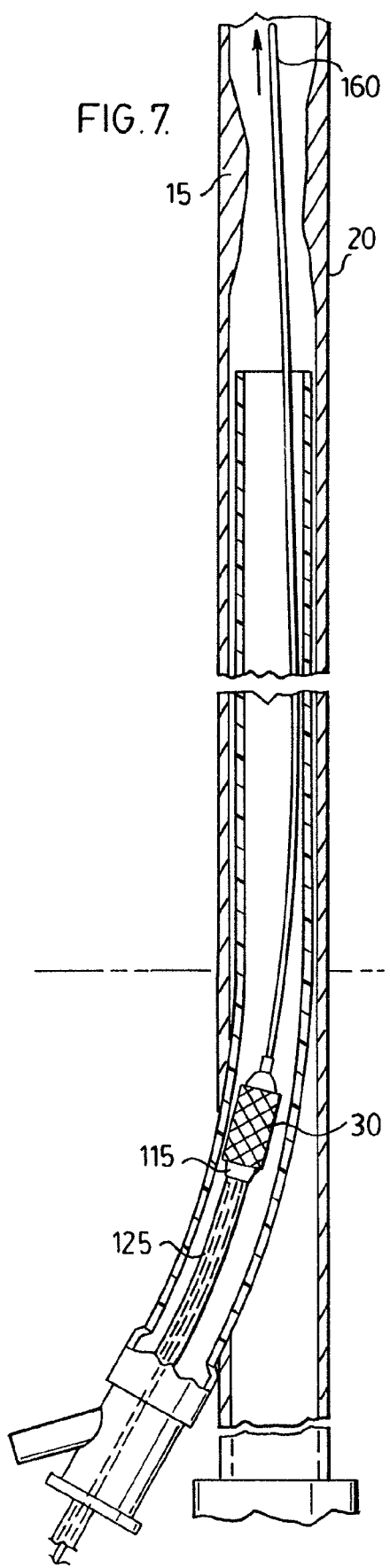

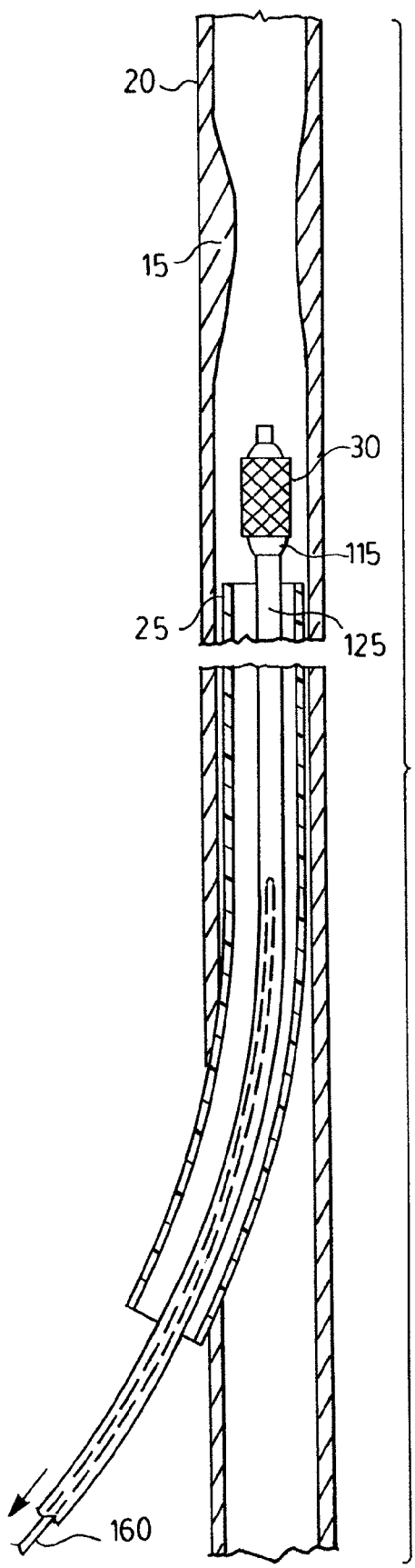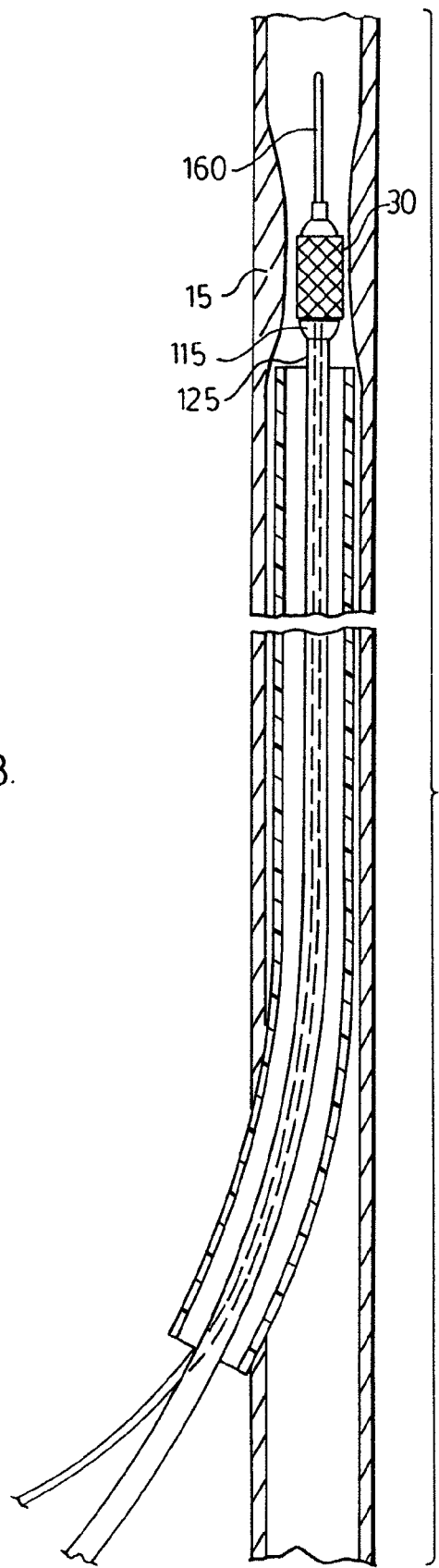

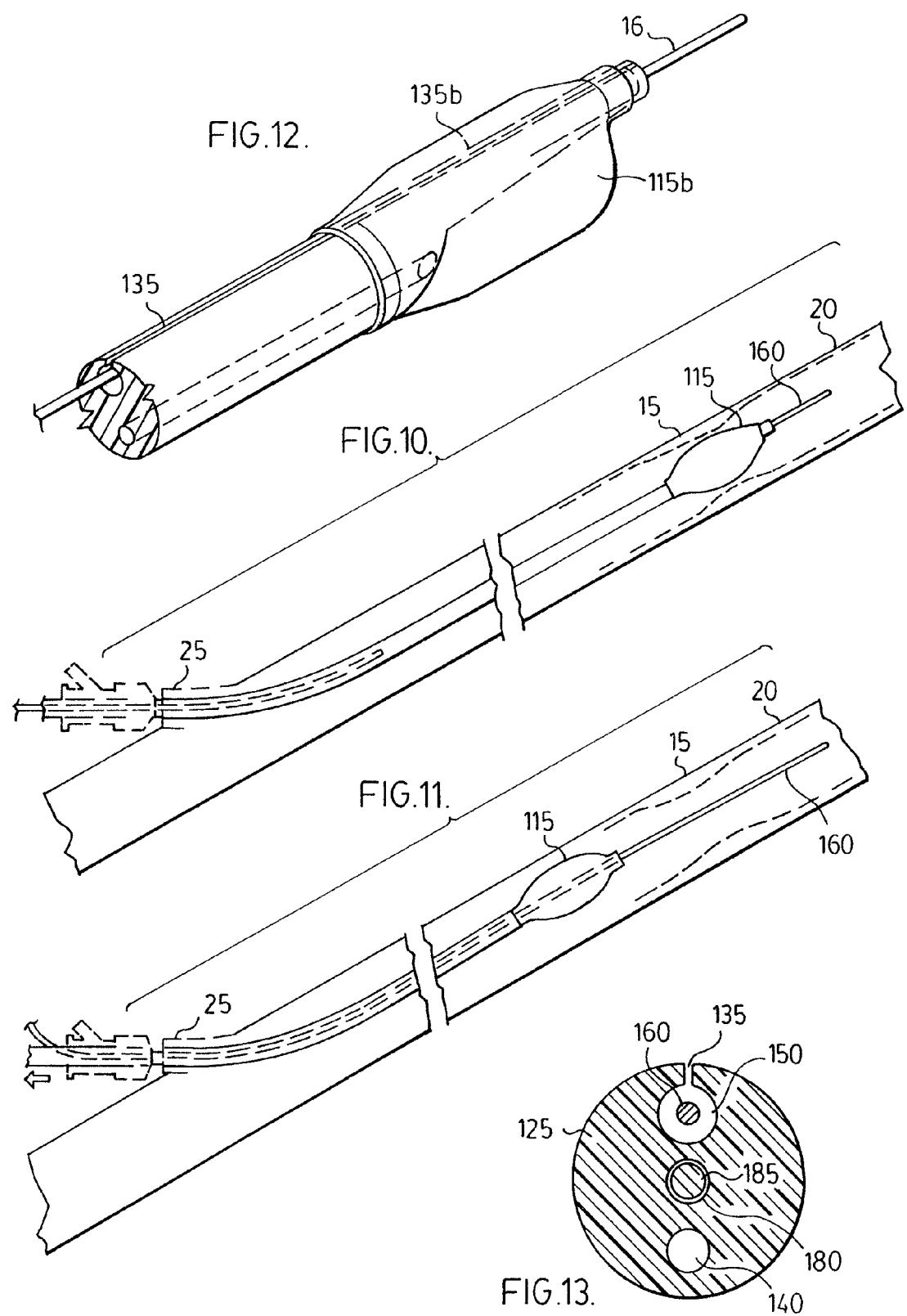

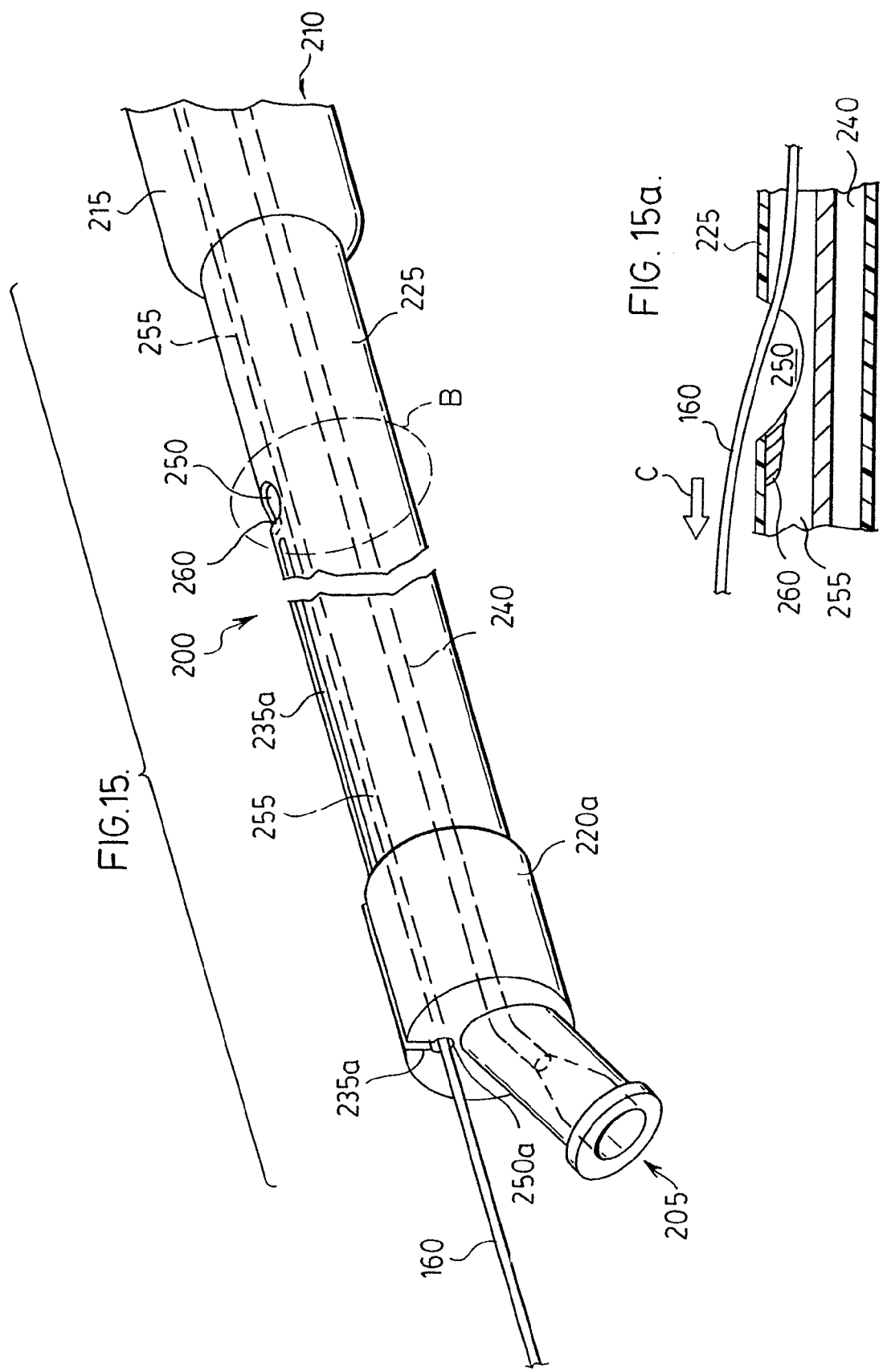

STENT DELIVERY SYSTEM AND METHOD OF USE

This application is a continuation of U.S. patent application Ser. No. 11/045,134, filed Jan. 31, 2005, which is a continuation of U.S. patent application Ser. No. 09/780,940, filed Feb. 12, 2001, now U.S. Pat. No. 6,849,077, issued Feb. 1, 2001, which is a continuation-in-part of U.S. patent application Ser. No. 09/557,007, filed Apr. 20, 2000 (now abandoned), which is a continuation-in-part of U.S. patent application Ser. No. 09/501,981, filed Feb. 11, 2000 (now abandoned), incorporated herein by reference.

BACKGROUND OF THE INVENTION

1. Field of the Invention

In one of its aspects, the present invention relates to a balloon dilation catheter. In another of its aspects, the present invention relates to a catheterization method.

2. Brief Description of the Prior Art

Balloon dilation catheters have been known for many years. Originally, such catheters were used in interventional techniques such as angioplasty.

In recent years, balloon dilation catheters have also been used to facilitate delivery of endovascular prosthesis' such as stents. Stents are generally known. Indeed, the term "stent" has been used interchangeably with terms such as "intraluminal vascular graft" and "expansible prosthesis". As used throughout this specification, the term "stent" is intended to have a broad meaning and encompasses any expandable prosthetic device for implantation in a body passageway (e.g., a lumen or artery).

In the past dozen years, the use of stents has attracted an increasing amount of attention due to the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire structure of the stent so that the latter is urged in place against the body passageway. As indicated above, the amount of force applied is at least that necessary to expand the stent (i.e., the applied force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

See, for example, any of the following patents:

U.S. Pat. No. 4,323,071 (Simpson et al.),
U.S. Pat. No. 4,411,055 (Simpson et al.),
U.S. Pat. No. 4,616,648 (Simpson),
U.S. Pat. No. 4,661,094 (Simpson),
U.S. Pat. No. 4,733,665 (Palmaz),
U.S. Pat. No. 4,739,762 (Palmaz),
U.S. Pat. No. 4,800,882 (Gianturco),
U.S. Pat. No. 4,907,336 (Gianturco),
U.S. Pat. No. 5,035,706 (Gianturco et al.),
U.S. Pat. No. 5,037,392 (Hillstead),
U.S. Pat. No. 5,041,126 (Gianturco),
U.S. Pat. No. 5,092,873 (Simpson et al.),
U.S. Pat. No. 5,102,417 (Palmaz),
U.S. Pat. No. 5,147,385 (Beck et al.),
U.S. Pat. No. 5,269,793 (Simpson),
U.S. Pat. No. 5,282,824 (Gianturco),
U.S. Pat. No. 5,316,023 (Palmaz et al.),
U.S. Pat. No. 5,415,634 (Glynn et al.),
U.S. Pat. No. 5,462,529 (Simpson et al.),
U.S. Pat. No. 5,755,771 (Penn et al.),
U.S. Pat. No. 5,980,570 (Simpson),
International patent application PCT/CA97/00151 (Penn et al.), and
International patent application PCT/CA97/00152 (Penn et al.), for a discussion on previous stent designs and deployment systems.

Given the development of stent design, the prior art has also focussed on delivery systems for stent deployment.

One particular delivery system is taught by U.S. Pat. No. 4,748,982 [Horzewski et al. (Horzewski)]. Horzewski teaches a reinforced balloon dilation catheter with a slitted exchange sleeve. Essentially, the catheter comprises a tubular member having a first lumen and a second lumen. A dilation balloon is mounted on the distal end of the tubular member and is in communication with the first lumen. An opening (or notch) is disposed in the tubular member intermediate its proximal and distal ends for receiving a guidewire which travels through the second lumen and emanates out of the distal end of the tubular member. A slit is disposed on the longitudinal portion of the tubular member between the opening and an area 0.5-1 cm proximal the dilation balloon. Thus, as illustrated in FIG. 1 of Horzewski, the guidewire travels partly within a lumen in the catheter (approximately 10-15 cm) and partly along the outside of the catheter (approximately 80-90 cm). This approach is also known as a "monorail" delivery system. The principal advantage of this approach is that it permits so-called "rapid exchange" of the balloon catheter with another balloon catheter. In design, the exchange is facilitated by the provision of the above-mentioned slit so that the actual exchange is done over the balloon portion only (approximately 3 cm). The principal disadvantages of this approach include: less than optimum steerability of the guidewire, difficulties in moving the guidewire with respect to the catheter, less than optimum torque control and inability to exchange the guidewire while leaving the catheter in place. The catheter illustrated by Horzewski has not gained widespread commercial popularity.

Another approach for catheterization is the so-called "over the wire" approach—this approach is discussed in many of the above-mentioned United States patents naming John P. Simpson as an inventor. In this approach, the catheter comprises a tubular member having a first lumen and a second lumen. A dilation balloon is mounted on the distal end of the tubular member and is in communication with the first lumen. The second lumen runs through the length of the tubular member. An opening is disposed in the tubular member at its proximal end for receiving a guidewire which travels through second lumen and emanates out of the distal end of the tubular member. Thus, in the "over the wire" approach, the guidewire is encompassed by the second lumen along the entire length of the tubular member (approximately 90-105 cm). The principal advantages of the this approach include: optimum steerability, smoother movement of the guidewire with respect to the catheter (due to the coaxial relationship thereof), optimum torque control and the ability to exchange the guidewire while leaving the catheter in place. The principal is disadvantage of this approach is that exchange with another balloon catheter is relatively cumbersome (i.e., compared to the "monorail" approach discussed above.

A purported improvement over the "monorail" delivery system is described in U.S. Pat. No. 5,195,978 [Schiffer]. Schiffer teaches a "rapid exchange over-the-wire catheter". The purported point of novelty in Schiffer is the provision of one or more breakaway elements for progressively exposing the guidewire from the proximal end toward the distal end of the catheter. In the illustrated embodiment the breakaway element is a pull tab or tear strip. The tab strip form from a plurality of longitudinally extending generally parallel grooves form in the tubular shaft of the catheter. The Schiffer catheter is disadvantageous since it requires the physician to execute two distinct and sequential steps to achieve "rapid exchange". First, the physician must take one hand off the guidewire or the catheter and thereafter grasp and remove the pull tab or tear strip to expose the guidewire. Second, the physician must remove the catheter while the guidewire is held in position. The requirement for these two distinct and sequential steps renders the Schiffer catheter cumbersome, time consuming and impractical to use.

Accordingly, it would be desirable to have a balloon dilation catheter which combined the advantages of the above-mentioned "monorail" approach and "over the wire" approach while obviating or mitigating the disadvantages of these approaches. It would be further advantageous if the balloon dilation catheter were readily adaptable to be used in various interventional techniques such as endovascular prosthesis delivery, angioplasty and the like.

SUMMARY OF THE INVENTION

It is an object of the present invention to provide a novel balloon dilation catheter.

It is another object of the present invention to provide a novel catheterization method.

Accordingly, in one of its aspects, the present invention provides a balloon dilation catheter comprising: a tubular member having a proximal end and a distal end;

an inflatable balloon disposed at the distal end of the tubular member;

a first lumen disposed in the tubular member and in communication with an interior of the inflatable balloon;

a second lumen disposed in the tubular member for receiving a guidewire along at least a portion its length (preferably the entire length), the second lumen having a first opening in the proximal region of the tubular member and a second opening at the distal region of the tubular member; and a first slit disposed longitudinally in the tubular member and extending along at least a portion of the tubular member, the first slit comprising a first pair of longitudinal edges in a side by side relationship, the tubular member being constructed of a resilient material such that, as the guidewire is separated from the second lumen, the longitudinal edges are biassed open from a first position to a second position having a gap greater than or equal a diameter of the guidewire.

In another of its aspects, the present invention provides a balloon dilation catheter comprising:

a tubular member having a proximal end and a distal end;
an inflatable balloon disposed at the distal end of the tubular member;
a first lumen disposed in the tubular member and in communication with an interior of the inflatable balloon;
a second lumen disposed in the tubular member for receiving a guidewire along a portion of its length (preferably the entire length), the second lumen having a first opening in the proximal region of the tubular member and a second opening at the distal region of the tubular member;
a first slit disposed longitudinally in the tubular member and extending along at least a portion of the tubular member, the slit permitting withdrawal of the guidewire from the second lumen; and
an adapter attached to the proximal region of the tubular member, the adaptor comprising a valve comprising a second slit and third lumen for receiving the guidewire, the second lumen and the third lumen in communication with one another, the second slit comprising a pair of longitudinal edges in a side by side relationship, the valve being constructed of a resilient material such that, as the guidewire is separated from the third lumen, the longitudinal edges are biassed open from a first position to a second position having a gap greater than or equal to a diameter of the guidewire.

Thus, the present inventor has discovered a balloon catheter which combines the advantages of the "over the wire" approach (i.e., optimum steerability, smoother movement of the guidewire with respect to the catheter (due to the coaxial relationship thereof), optimum torque control and the ability to exchange the guidewire while leaving the catheter in place) with the principal advantage of the "monorail" approach (i.e., rapid exchange of the balloon catheter with another balloon catheter while leaving the guidewire in place).

As used throughout this specification, the term "tubular member", when used in the context of the present balloon dilation catheter is intended to mean a portion of the catheter generally tubular in construction and generally representing the large majority of the overall length of the balloon dilation catheter. Typically, the tubular member will be at least about 75%, more preferably at least about 85%, most preferably at least about 95%, of the overall length of the balloon dilation catheter.

Thus, the present inventor has discovered a balloon dilation catheter which have one or more of the number of novel features. For example, it has been discovered that a particularly advantageous approach in facilitating guidewire removal from the catheter is to utilize materials for the tubular member which, when finely slitted, results in the longitudinal edges of the slit portion being abutting or touching engagement. This obviates or mitigates back bleeding through that portion of the catheter which is outside the patient during use. Another independently novel feature of the present balloon dilation catheter is the adapter located at the proximal end of the catheter. Specifically, the present inventor has discovered that the use of resilient valve in the adapter having a slit disposed therein (preferably aligned with the slit in the tubular member) allows for advantageous removal of the guidewire from balloon dilation catheter while obviating or mitigating unintended or accidental removal of the guidewire or damage thereto.

BRIEF DESCRIPTION OF THE DRAWINGS

Embodiments of the present invention will be described with reference to the accompanying drawings wherein like numerals designate like parts and in which:

FIG. 1 illustrates a perspective view of an embodiment of the present balloon dilation catheter;

FIG. 2 is a sectional view along line II-II in FIG. 1;

FIG. 3 is a sectional view along line III-III in FIG. 1;

FIG. 4 illustrates an exploded view of modified proximal end of the balloon dilation catheter illustrated in FIG. 1;

FIGS. 5-11 illustrate steps in various catheterization techniques employing the present balloon dilation catheter;

FIG. 12 illustrates a modified balloon for use in the present balloon dilation catheter;

FIG. 13 illustrates a preferred embodiment of a-modified tubular member for use in the present balloon dilation catheter;

FIG. 15 illustrates an alternate embodiment of the balloon dilation catheter illustrated in FIG. 4;

FIG. 15a is an enlarged sectional view of region B of FIG. 15; and

DETAILED DESCRIPTION OF THE PREFERRED EMBODIMENTS

Figure 5:
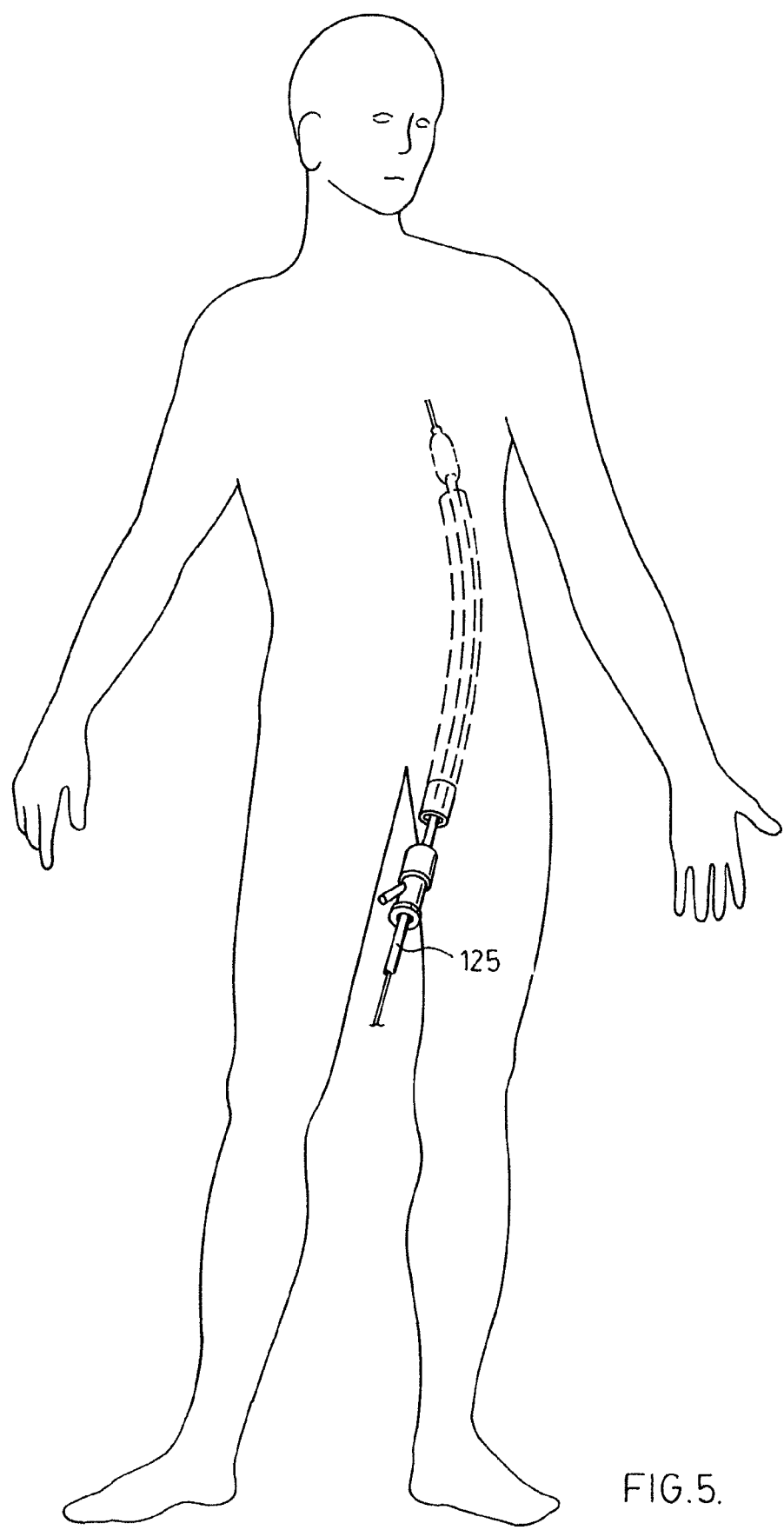

Thus, with reference to FIGS. 1-3, there is illustrated a balloon dilation catheter 100. Balloon dilation catheter 100 comprises a proximal end 105 and a distal end 110. Distal end 110 of balloon dilation catheter 100 comprises an expandable balloon 115. Proximal end 105 of balloon dilation catheter 100 comprises an single lumen Luer-type adaptor 120. Disposed between adaptor 120 and balloon 115 is a tubular member 125.

As will be apparent from FIG. 1, disposed in tubular member 125 is an opening 130. Also disposed in tubular member 125 is a slit 135 which extends from opening 130 to a point in tubular member 125 just proximal balloon 115.

With particular reference to FIGS. 2 and 3, tubular member 125 comprises a first lumen 140 and a second lumen 150. First lumen 140 is designed to be in communication with an interior of balloon 115. The design of the interface between balloon 115 and first lumen 140 is conventional—see for example Horzewski referred to hereinabove. The construction of tubular member 125 having opening 130, slit 135, first lumen 140 and second lumen 150 is conventional—see Horzewski referred to hereinabove.

With further reference to FIGS. 1-3, it will be apparent that opening 130 is designed to receive a guidewire 160. Guidewire 160 passes through second lumen 150 and out of a distal opening of tubular member 125 beyond balloon 115.

Preferably, slit 135 has a width which is less than the diameter of guidewire 160. In a more preferred embodiment, the longitudinal edges of slit 135 are abutting or touching engagement thereby proving containment of guidewire 160 therein. Slit 135 maybe formed by an suitable means, including the use of a very thin slicing member being run longitudinally along the surface of tubular member 125 corresponding to second lumen 150. Other manufacturing means will be apparent to those of skill in the art.

In FIG. 4, there is illustrated a modification of balloon dilation catheter 100 illustrated in FIGS. 1-3.

Specifically, in FIG. 4, Luer-type adaptor 120a is modified to contain a lumen 150a in communication with a slit 135a. As will be apparent to those of skill in the art, lumen 150a is in communication with second lumen 150 in tubular member 125. Further, slit 135a is in communication with slit 135 in tubular member 125. The modification of balloon dilation catheter 100 illustrated in FIG. 4 eliminates the need for having opening 130 disposed in tubular member 125 illustrated in FIG. 1.

With reference to FIGS. 5-9, the delivery of balloon dilation catheter 100 will be described.

As is known in the art, catheterization is normally performed to alleviate a lesion in an artery. This is shown schematically in FIGS. 6-9 wherein a lesion in the form of a blockage 15 obstructs an artery 20. In certain cases, it is desirable to deploy a stent at the site of the lesion to maintain the patency of artery 20 at the site of blockage 15. As shown in FIG. 5, catheterization is performed through an incision in the groin area of the patient.

Thus, with reference to FIGS. 6 and 7, a guide catheter 25 is initially delivered into artery 20 to a region proximal of blockage 15. The proximal end of guide catheter 25 remains outside the patient.

Balloon dilation catheter 100 (FIG. 1) has mounted on balloon 115 thereof a stent 30. Further, guidewire 160 is disposed in second lumen 150 such that it emanates from opening 130 and from distal end 110 of balloon dilation catheter 100. Preferably, this is achieved in a conventional manner by feeding guidewire 160 into second lumen 150 at distal end 110 of balloon dilation catheter 100 until the proximal end of guidewire 160 emanates from opening 130.

At this point, balloon dilation catheter 100 is inserted into guide catheter 25 and guidewire 160 is navigated through artery 20 to a point distally of blockage 15 (FIG. 7).

Alternatively, it is possible to advance guidewire 160 to a point distally of blockage 15, a f t e r which the distal end of second lumen 150 of balloon dilation catheter 100 is passed onto the proximal end of guidewire 160. If it becomes difficult to advance guidewire 160 across blockage 15 using this technique, it is possible to advance balloon dilation catheter 100 over the proximal end of guidewire 160 until that end exits opening 130 and the system may used in the "over-the-wire" approach described herein.

In FIG. 8, there is illustrated removal of guidewire 160 while leaving balloon dilation catheter 100 in position at point proximal to blockage 15. This is an advantageous feature of the present balloon dilation catheter which is not possible with the balloon dilation catheter taught in Horzewski. Thus, guidewire 160 may simply be replaced with another guidewire by removing the original guidewire from proximal end 105 of balloon dilation catheter 100 and simply inserting a replacement guidewire (not shown) into the proximal end 105 of balloon dilation catheter 100 and through tubular member 125. Thereafter, the replacement guidewire may be navigated so that it emanates from distal end 110 of balloon dilation catheter 100. The replacement guidewire is navigated to a point distal of blockage 15.

Balloon dilation catheter 100 is then navigated over the replacement guidewire such that stent 30 is in proper position with respect to blockage 15 (FIG. 8). Once the guidewire and balloon dilation catheter 100 are in the correct position, fluid is injected into first lumen 150 thereby expanding balloon 115 and stent 30 mounted thereon. Deployment of a stent in this manner is conventional and within the purview of a person skilled in the art.

In FIGS. 10 and 11, there is illustrated rapid exchange of balloon dilation catheter 100 while leaving guidewire 160 in place. In this case, for clarity, stent 30 is not shown on balloon 115. One of the features of the present balloon dilation catheter which distinguishes it from that in Horzewski is that guidewire 160 emanates from a proximal portion of balloon dilation catheter 100 which is always outside the body of the patient. This provides the practitioner with the "over-the-wire" approach described above. Thus, either opening 130 is located outside the body at all times during use of catheter 100 illustrated in FIG. 1 or it is necessarily emanating from the proximal end of balloon dilation catheter 100 if the modified embodiment in FIG. 4 is utilized.

When it is desired to exchange balloon dilation catheter 100, the balloon dilation catheter is withdrawn from artery 20 while leaving guidewire 160 in place. As balloon dilation catheter 100 is withdrawn from the body of the patient, it may be readily separated from guidewire 160 via slit 135 along virtually the entire length of tubular member 125—this is one of the principal advantages of the present balloon dilation catheter which, to the knowledge of the present inventors, has not been achieved with a prior balloon dilation catheter. Once distal end 110 of balloon dilation catheter 100 is withdrawn from the body, balloon 115 may be exchanged from guidewire 160 in a conventional manner.

A replacement balloon dilation catheter may then be fed over guidewire 100 and navigated into artery 20 in the area of blockage 15.

With reference to FIG. 12, there is illustrated yet a further alternate embodiment to the present balloon dilation catheter. In this case, a slit 135b is provided in balloon 115b such that slit 135 is in communication with slit 135b on balloon 115b. This modification of balloon catheter 100 is particularly advantageous when the catheter is being used in an angioplasty application (i.e., without a stent mounted on balloon 115) as a pre-dilation balloon catheter allowing for enhanced rapid exchange features by facilitating withdrawal of guidewire 160 in a rapid exchange manner along virtually the entire length of tubular member 125 and balloon 115b via the combination of slits 135 and 135b. This feature is generally advantageous since it facilitates withdrawal of the balloon dilation catheter from the patient.

With reference to FIG. 13, there is illustrate a preferred modification to tubular member 125 of balloon catheter 100. Specifically, a third lumen 180 is provided along substantially the entire length of tubular member 125. Disposed within third lumen 180 is a stiffening member 185 which serves to improve the "torqueability" of balloon dilation catheter. Unlike, the approach in Horzewski described above wherein a single lumen does double duty for receiving: (i) a stiffening member along most of the length of the catheter and (ii) the guidewire along a minor portion of its length, the approach shown in FIG. 13 is a significant improvement over Horzewski since it maximizes both the distance over which rapid exchange may be effected and the distance over which stiffening may be conferred to the tubular member.

Figure 14A:
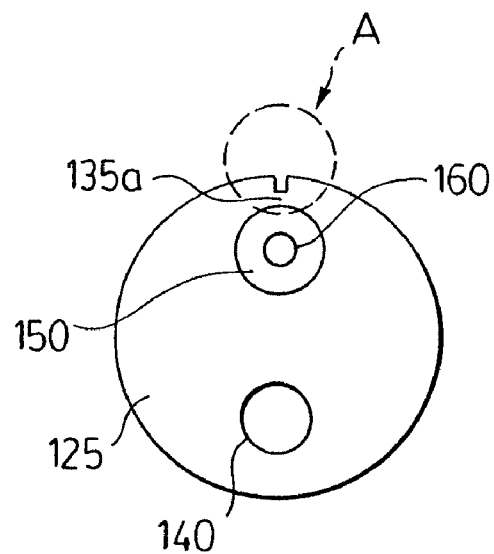
FIGS. 14a, 14b and 14c illustrate preferred embodiments of a modified tubular member for use in the present balloon dilation catheter.
Figure 14B:
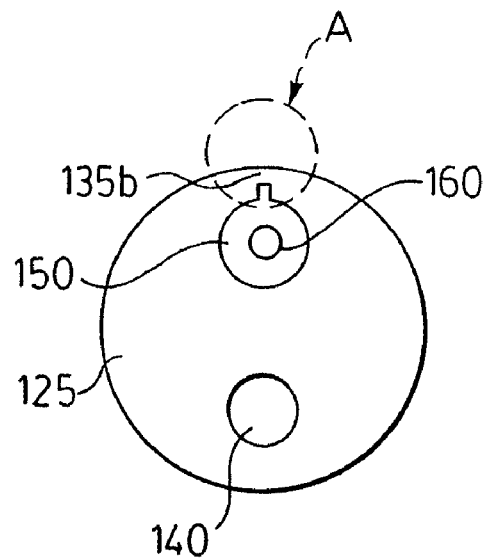
Figure 14C:
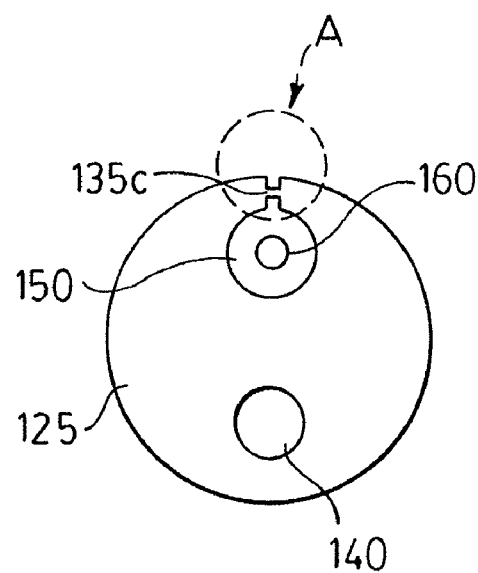

With reference to FIGS. 14a, 14b and 14c, there is illustrated a modification to the balloon dilation catheter illustrated in FIGS. 1-3 and described hereinabove. In FIGS. 1-3 and 14a, 14b and 14c, like numerals designate like elements. As will be evident tubular member 125 has been modified to provide a weakened region A. Weaken region A comprises a thinned wall 135a (FIG. 14a), 135b (FIG. 14b) and 135c (FIG. 14c). When it is desired to exchange balloon catheter 100, guidewire 160 is separated from tubular member 125. The separation force causes incision of thinned wall 135a (FIG. 14a), 135b (FIG. 14b) and 135c (FIG. 14c). This causes in situ formation of a slit as guidewire 160 is separated from tubular member 125. The feature of in situ slit formation is a significant advantage over the Schiffer catheter design above since, in this embodiment of the present balloon dilation catheter, in situ slit formation and guidewire separation from the tubular member are achieved simultaneously in a one-step operation. Additionally, provision of thinned wall 135a (FIG. 14a), 135b (FIG. 14b) and 135c (FIG. 14c) obviates or mitigates reduction in the integrity of tubular member 125 since a slit is not formed therein until the guidewire is removed (i.e., until a point in time after the catheter has been navigated to the target location).

With reference to FIG. 15, there is illustrated a modification of balloon dilation catheter 100 illustrated in FIGS. 1-4.

Specifically, in FIG. 15, there is illustrated a balloon dilation catheter 200 comprising a proximal end 205 and a distal end 210. Distal end 210 of balloon dilation catheter 100 comprises an expandable balloon 215. Proximal end 205 of balloon dilation catheter 200 comprises adapter 220a which is similar to adapter 120a in FIG. 4. Disposed between adapter 220a and balloon 215 is a tubular member 225. As will be apparent from FIG. 15, disposed in tubular member 225 is a slit 235. Slit 235 is similar to slit 135 in FIG. 4 with the exception that slit 235 ends at a spot more proximally than slit 135. Disposed distally of slit 235 is a port or an opening 250 which is in communication with a guidewire receiving lumen 255 extending along the entire length of tubular member 225 and through the distal end of balloon 215. Disposed at the distal region of opening 250 is a ramp 260 whose function will be described below.

Ramp 260 may be formed by any suitable means. In one preferred embodiment, ramp 260 is formed in situ by piercing the outer wall of tubular member 225 on a surface corresponding to guidewire lumen 255 using a hot instrument which results in formation of small mass on the inside surface of guidewire lumen 255 in the form of ramp 260. Again, other suitable means for manufacturing ramp 260 will be apparent to those of skill in the art.

Balloon dilation catheter 200 may be used in the following manner.

The initial steps of using balloon dilation catheter 200 are similar to those described above in relation to the use of balloon dilation catheter 100. Thus, once the balloon dilation catheter 200 has been withdrawn it is to be replaced with another balloon dilation catheter, the replacement balloon dilation catheter may be a conventional "monorail"-type balloon dilation catheter such as the one taught in Horzewski or balloon dilation catheter 200. Specifically, with reference to FIGS. 15 and 15a, balloon dilation catheter 200 is fed over guidewire 160 in the direction of arrow C. Once the proximal end of guidewire 160 approaches the area in guidewire lumen 255 corresponding to opening 250, it is biassed upwardly and outwardly from opening 250 by ramp 260, thereby rendering the replacement catheter 200 a "monorail"-type catheter. As stated above, the replacement catheter could be a conventional "monorail"-type catheter.

Figure 16:
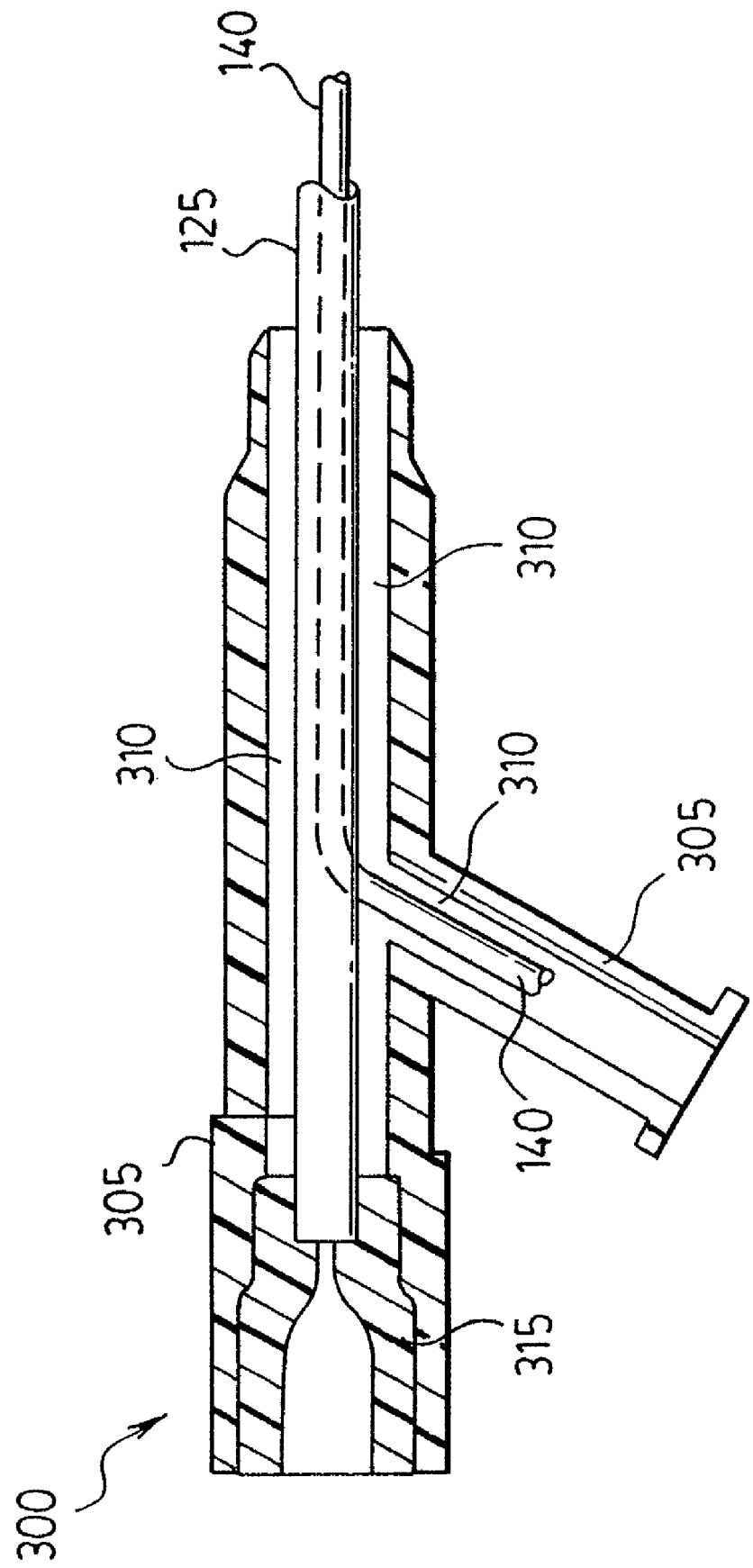
FIG. 16 illustrates a preferred embodiment of an adapter at the proximal end of the present balloon dilation catheter.

With reference to FIG. 16, there is illustrated an adapter 300 which is particularly preferred for use in the present balloon dilation catheter. Thus, adapter 300 comprises an outer housing 305, typically constructed from plastic or other durable material. Tubular member 125 as described above in relation to FIG. 1-4 is disposed within housing 305 as illustrated and is sealed with respect to housing 305 by adhesive 310 or any other suitable adhesive/sealant material. As illustrated, first lumen 140 which is in communication with the interior of the balloon (not shown) of the catheter, emminates from tubular member 125 into a first arm 305 of adapter 300. This proximal end of first lumen 140 is then able to receive injection fluid to inflate the balloon.

Disposed at the proximal end of adapter 300 within housing 305 is a resilient valve 315. Resilient valve 315 may be made out of a polymeric material based on silicone and the like. This resiliency is particularly beneficial since the formation of a slit in valve 315 allows the edges of the slit to be abutting or touching engagement until such time as the guidewire is to be removed—indeed the view in FIG. 16 is a sectional view taken along the slit (not shown as such). As the guidewire is removed, it biases open the slit in resilient valve 315. After removal of the guidewire since valve 315 is made from a resilient material, the slit "closes" that the edges thereof are abutting or touching engagement (or a gap less than the diameter of the guidewire separates the edges). The advantages from this approach include: mitigating or obviating back bleeding through the catheter, mitigating or obviating unintentional displacement of the guidewire form adapter 300 and the like.

While this invention has been described with reference to illustrative embodiments, this description is not intended to be construed in a limiting sense. For example, while the illustrated embodiments depict use of the present balloon dilation catheter in delivery of a stent, those of skill in the art will immediately appreciate that the present balloon dilation catheter may be used in percutaneous transluminal coronary angioplasty techniques. Further, as will be apparent to those of skill in the art, it is possible to combine, in a single catheter, the slit illustrated in FIGS. 1-3 with the weakened region illustrated in FIGS. 14a, 14b and/or 14c. Further, while preferred, it is not strictly necessary for the weakened region illustrated in FIGS. 14a, 14b and/or 14c to extend along substantially the entire length of the tubular member. Still further, the specific nature of the weakened region illustrated in FIGS. 14a, 14b and 14c is not particularly restricted provided that it can be readily incised as the guidewire separated from the catheter—e.g., a perforated region or a region comprising a plurality of small, partial cuts is also useful. Still further, it is possible to modify tubular member 125 such that one of lumen 140 and lumen 150 comprises a passageway having a substantially circular shaped cross-section while the other comprises a passageway having a substantially semi-circular shaped cross-section. Various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A balloon dilation catheter comprising:
   a tubular member having a proximal end and a distal end;
   an inflatable balloon disposed at the distal end of the tubular member;
   a first lumen disposed in the tubular member and in communication with an interior of the inflatable balloon;
   a second lumen disposed in the tubular member for receiving a guidewire along at least a portion of its length, the second lumen having a first opening in a proximal region of the tubular member;
   a first slit disposed longitudinally in the tubular member and extending along at least a portion of the tubular member, the first slit comprising a first pair of longitudinal edges in a side by side relationship, the tubular member being constructed of a resilient material such that, as the guidewire is separated from the second lumen, the longitudinal edges are biased open from a first position to a second position having a gap greater than or equal a diameter of the guidewire, wherein the second lumen: (i) further comprises a second opening disposed between a distal end of the first slit and the inflatable balloon, and (ii) is circumferentially continuous in the region of the tubular member between the second opening and the inflatable balloon; and
   an adapter attached to the proximal region of the tubular member, the adaptor comprising a valve having a second slit and third lumen for receiving the guidewire, the second lumen and the third lumen in communication with one another, the second slit being narrower than the maximum dimension of the third lumen.

2. The balloon dilation catheter defined in claim 1, wherein, in the first position, the first pair of longitudinal edges are in an abutting relationship.

3. The balloon dilation catheter defined in claim 1, wherein, in the first position, the first pair of longitudinal edges are in spaced relationship, a space between the longitudinal edges being less than the diameter of the guidewire.

4. The balloon dilation catheter defined in claim 1, wherein the first slit extends from the first opening to adjacent the second opening.

5. The balloon dilation catheter defined in claim 1, wherein the second slit comprises a second pair of longitudinal edges in a side by side relationship, the valve being constructed of a resilient material such that, as the guidewire is separated from the third lumen, the second pair of longitudinal edges are biased open from a first position to a second position having a gap greater than or equal a diameter of the guidewire.

6. The balloon dilation catheter defined in claim 5, wherein, in the first position, the second pair of longitudinal edges are in an abutting relationship.

7. The balloon dilation catheter defined in claim 5, wherein, in the first position, the second pair of longitudinal edges are in spaced relationship, a space between the longitudinal edges being less than the diameter of the guidewire.

8. The balloon dilation catheter defined in claim 1, wherein the first slit and the second slit are in substantial longitudinal alignment.

9. The balloon dilation catheter defined in claim 1, wherein the inflatable balloon includes a third slit in substantial alignment with the first slit.

10. The balloon dilation catheter defined in claim 1, wherein the tubular member comprises a fourth lumen for receiving a stiffening member.

11. The balloon dilation catheter defined in claim 10, further comprising a stiffening member disposed in the third lumen.

12. The balloon dilation catheter defined in claim 1, wherein the first lumen and the second lumen each comprise a passageway having a substantially circular cross-section, both disposed in a substantially solid tubular member.

13. The balloon dilation catheter defined in claim 1, wherein one of the first lumen and the second lumen comprises a passageway having a substantially circular shaped cross-section disposed in a substantially solid tubular member, and the other lumen comprises a passageway having a substantially semi-circular shaped cross-section disposed in a substantially solid tubular member.

14. The balloon dilation catheter defined in claim 1, wherein the first slit extends along a proximal portion of the length of the tubular member.

15. The balloon dilation catheter defined in claim 1, wherein the second opening comprises a ramp to direct a proximal end of the guidewire through the second opening as the guidewire is moved proximally in the second lumen.

16. A catheterization kit comprising:
    a guide catheter;
    a tubular member having a proximal end and a distal end;

an inflatable balloon disposed at the distal end of the tubular member;

a first lumen disposed in the tubular member and in communication with an interior of the inflatable balloon;

a second lumen disposed in the tubular member for receiving a guidewire along at least a portion of its length, the second lumen having a first opening in a proximal region of the tubular member;

a first slit disposed longitudinally in the tubular member and extending along at least a portion of the tubular member, the first slit comprising a first pair of longitudinal edges in a side by side relationship, the tubular member being constructed of a resilient material such that, as the guidewire is separated from the second lumen, the longitudinal edges are biased open from a first position to a second position having a gap greater than or equal a diameter of the guidewire, wherein the second lumen: (i) further comprises a second opening disposed between a distal end of the first slit and the inflatable balloon, and (ii) is circumferentially continuous in the region of the tubular member between the second opening and the inflatable balloon; and an adapter attached to the proximal region of the tubular member, the adaptor comprising a valve having a second slit and third lumen for receiving the guidewire, the second lumen and the third lumen in communication with one another, the second slit being narrower than the maximum dimension of the third lumen.

17. A stent-mounted balloon catheter comprising: a tubular member having a proximal end and a distal end;

an inflatable balloon disposed at the distal end of the tubular member;

a first lumen disposed in the tubular member and in communication with an interior of the inflatable balloon;

a second lumen disposed in the tubular member for receiving a guidewire along at least a portion of its length, the second lumen having a first opening in a proximal region of the tubular member;

a first slit disposed longitudinally in the tubular member and extending along at least a portion of the tubular member, the first slit comprising a first pair of longitudinal edges in a side by side relationship, the tubular member being constructed of a resilient material such that, as the guidewire is separated from the second lumen, the longitudinal edges are biased open from a first position to a second position having a gap greater than or equal a diameter of the guidewire, wherein the second lumen: (i) further comprises a second opening disposed between a distal end of the first slit and the inflatable balloon, and (ii) is circumferentially continuous in the region of the tubular member between the second opening and the inflatable balloon;

an adapter attached to the proximal region of the tubular member, the adaptor comprising a valve having a second slit and third lumen for receiving the guidewire, the second lumen and the third lumen in communication with one another, the second slit being narrower than the maximum dimension of the third lumen; and a stent mounted on the inflatable balloon of the catheter.

* * * * *